United States Patent [19]

Kornerup

[11] Patent Number: 4,974,917
[45] Date of Patent: Dec. 4, 1990

[54] ELECTRODE PLATE

[76] Inventor: Niels Kornerup, Horkaer 34, DK-2730 Herlev, Denmark

[21] Appl. No.: 346,729

[22] Filed: May 3, 1989

[51] Int. Cl.$^5$ .............................................. A61N 1/04
[52] U.S. Cl. ..................................... 128/798; 128/802
[58] Field of Search .............. 128/640, 798, 800, 802, 128/419 D

[56] References Cited

U.S. PATENT DOCUMENTS

| | | | |
|---|---|---|---|
| 3,762,420 | 10/1973 | Moore et al. | 128/798 |
| 4,367,755 | 1/1983 | Bailey | 128/802 X |
| 4,458,696 | 7/1984 | Larimore | 128/798 |
| 4,827,939 | 5/1989 | Cartmell et al. | 128/640 |

FOREIGN PATENT DOCUMENTS 8500017  1/1985  PCT Int'l Appl. ................. 128/802

Primary Examiner—Lee S. Cohen

[57] ABSTRACT

An electrode plate for use in connection with a defibrillation electrode is described. The electrode plate comprises substantially coextending inter-connected first and second electrically conductive layers, said first layer comprising raised rim means defining an area within which a defibrillation electrode may be placed in electrically conductive contact with said first layer, said second layer being provided opposite to said rim means and comprising an adhesive for bringing said electrode plate into electrically conductive contact with a selected skin area, the overall extension of said electrode plate being such that when adhered to a selected skin area of a patient, a defibrillation electrode can be placed within the confines of said raised rim means without directly touching any skin portion. In this manner the desired contact is achieved without the use of messy creams or the like. In addition the advantage is obtained that the electrode plate maintains its conductive properties for a long time whereby it is possible to repeat the treatment very quickly, if necessary.

12 Claims, 1 Drawing Sheet

U.S. Patent                Dec. 4, 1990                4,974,917
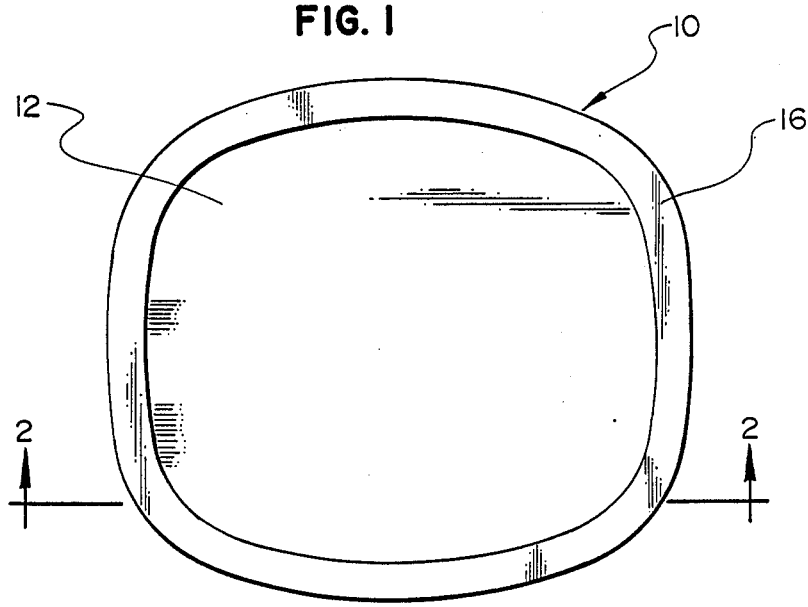
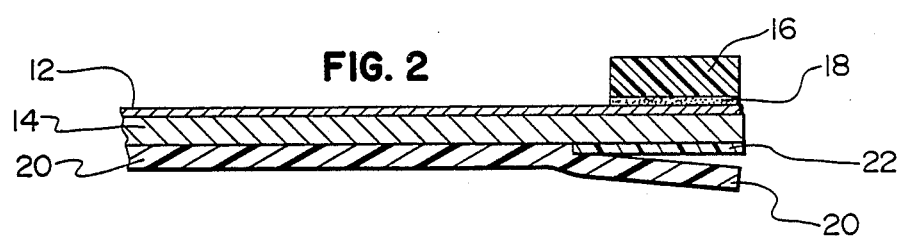
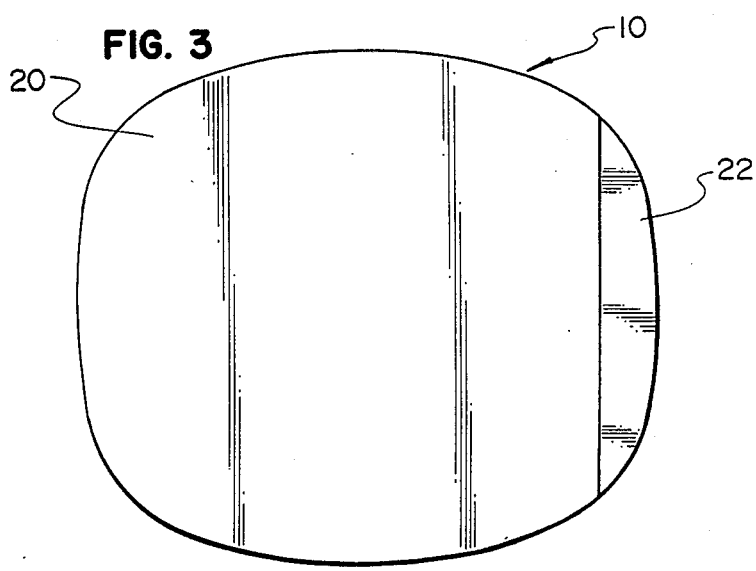
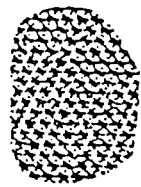

ELECTRODE PLATE

BACKGROUND OF THE INVENTION

This invention relates to an electrode plate for use in connection with a defibrillation electrode.

Several types of defibrillation electrodes for use in treatment of suspended heart action are already known. Such electrodes have a considerable extension and must be brought into conductive contact with the surface of the skin of a patient over a larger area. In order to provide good contact with the skin, it is common practice to smear the patient with a conductive gel or cream or to place a plate of a conductive gel on the patient prior to placing the electrodes. However, such gels are unpleasant to use because everything in the vicinity thereof gets messy.

SUMMARY OF THE INVENTION

It is an object of the invention to provide an electrode plate allowing the desired contact with the skin to be established in an easier manner than previously known.

According to the invention this object is achieved by an electrode plate comprising substantially coextending inter-connected first and second electrically conductive layers, said first layer comprising raised rim means defining an area within which a defibrillation electrode may be placed in electrically conductive contact with said first layer, said second layer being provided opposite to said rim means and comprising an adhesive for bringing said electrode plate into electrically conductive contact with a selected skin area, the overall extension of said electrode plate being such that when adhered to a selected skin area of a patient, a defibrillation electrode can be placed within the confines of said raised rim means without directly touching any skin portion.

In this manner an electrode plate is obtained which is easy to apply to the surface of the skin of a patient and which is correspondingly easy to remove. The plate provides a good contact with the skin because of the combination of the first electrically conductive, preferably metallic layer and the second electrically conductive, adhesive layer ensuring a good contact between the metallic layer and the skin of the patient. The metallic layer provides good contact for the defibrillation electrode, the usually plane metal surface of which is brought into direct contact with larger or smaller portions of the surface of the electrode plate.

The flexible nature of the electrode plate according to the invention and of the usually curved skin surface of the patient has the effect that under the pressure of the often rather heavy defibrillation electrodes the actual contact area between the two surfaces will be rather large, which is very important with regard to an efficient passage of current. As a result of the current-distributing effect of the conductive metallic layer the patient receives the electric shock through a large skin area, which is of importance for avoiding a burning of the patient. The raised rim ensures a suitable reinforcement of the metal sheet in such a manner that said sheet is not torn. In addition the raised rim ensures that the defibrillation electrode cannot slip and come into direct contact with the skin, which in such case could get seriously burnt. Finally, the feature that the two electrically conductive layers, i.e. the first preferably metallic layer and the second adhesive layer, are of substantially the same extension optimizes the utilization of the conductive properties of said layers in a direction perpendicular to their extension.

As previously mentioned, the first layer is preferably metallic, and according to a preferred embodiment it is a sheet of metal selected from tin, nickel, silver and aluminum or combinations thereof. Alternatively, the first layer may comprise conductive carbon fibres or consist of a conductive plastics having a conductive material embedded therein. The raised rim may be a strip of foam plastics and is preferably insulating.

The electrode plate according to the invention can be used in the following manner. Two plates are placed on the body of the patient at a location where it is desired to subject said patient to the electric revival treatment, i.e. on the chest typically in two areas called sternum and apex, or optionally one on the back and one on the chest. Two defibrillation electrodes f. inst. of a kind known in the art, are subsequently placed, one on each plate, in such a manner that the contact surface of the electrode makes contact with the conductive sheet of metal, said sheet of metal in turn being in contact with the body through the conductive adhesive layer. The defibrillation electrodes are connected to a defibrillator in a conventional manner. One of the advantages of the new electrode plates is that it can remain on the patient after the first revival, whereby possible recurrences can be quickly attended to. The possibility of the electrode remaining on the body presents considerable advantages over the known creams and gel plates as the creams and gel plates dry out rather quickly thereby loosing their electric conductivity. The conductive sheet of metal over the dermally-nonirritating adhesive layer has the effect that said layer maintains its humidity for a long time after the placing of the electrode plate on the skin of the patient.

The body facing side of the electrode plate, i.e. the gel side, is preferably covered by a protecting sheet of plastics or paper until the plate is brought into use.

BRIEF DESCRIPTION OF THE DRAWINGS

The invention is described in greater detail below with reference to the accompanying drawing, in which FIG. 1 illustrates an embodiment of an electrode plate according to the invention, FIG. 2 is an enlarged sectional view taken along the line II—II of FIG. 1, the layer thickness being highly exaggerated, FIG. 3 is a rear view of the electrode plate of FIG. 2, and FIG. 4 illustrates a portion of the surface of the plate in natural size.

DESCRIPTION OF THE PREFERRED EMBODIMENTS

Referring to FIG. 1 illustrating a presently preferred embodiment of the invention, the electrode plate 10 comprises an electrically conductive layer 12, preferably being a sheet of metal, such as a tin sheet or an aluminum sheet, and an electrically conductive and adhesive, dermally-nonirritating gel or an electrically conductive, pressure sensitive adhesive layer 14 which may be of a known type.

According to a preferred embodiment, the sheet of metal and the gel plate are of the same extension and of a generally elliptic or circular shape, or possibly of a rectangular or other polygonal shape, preferably with rounded corners.

A raised, preferably closed rim 16 is placed on the conductive sheet 12, said rim defining an area wherein a defibrillation electrode can be placed when a patient is to be treated.

According to a preferred embodiment, the raised rim is a strip of a foamed plastics 16, said strip on one side being provided with an adhesive layer 18 adhering the strip 16 to the sheet of metal 12. The adhesive layer 18 may be a glue of known type.

The strip 16 is preferably placed along the edge of the sheet of metal 12 and the gel plate 14. As a result thereof the strip 16 also has a reinforcing effect on the edge, the sheet and the gel thereby being protected against being torn. The most important advantage gained by the strip 16 is, however, that said strip prevents a possible sliding of a defibrillation electrode, i.e. the rather large and heavy electrode which is connected to the defibrillator and which is to transfer the electric shock to the patient through the electrode plate 10 according to the invention.

A typical defibrillation electrode comprises a circular contact surface of a diameter of about 85 mm, and it is obvious that the extension of the conductive sheet 12 must be somewhat larger than the conductive contact surface of the defibrillation electrode. The electrode plate must be at least so large that the area of the conductive sheet of metal being defined within the raised rim is sufficiently large for receiving the contact surface of the defibrillation electrode.

It is within the scope of the invention to modify the illustrated embodiment, f.inst. by the raised rim formed by the strip 16 not being a continuously closed rim, and by the raised rim being placed somewhat inwardly from the edge of the conductive sheet 12, whereby a smaller area of the sheet is defined for the placing of the defibrillation electrode.

Until use the electroded plate is preferably protected by a releasable layer 20 of paper or plastics which is peeled off immediately before the electrode plate is placed on a patient. In this manner the electrically conductive and adhesive properties of the layer 14 are maintained.

Furthermore, a section of the dermally-nonirritating adhesive layer 14 being located along an edge portion of said layer is preferably covered by a sheet 22 of plastics or paper presenting a non-sticky exposed surface and preferably being in a strong colour easyly being seen. In this area the protecting layer 20 is loosely overlaying the strongly coloured sheet 22, which makes it easy to see where the peeling off of the protecting layer is to be initiated. It is also easy later on after termination of the treatment to remove the electrode plate from the patient without the operator coming into contact with the adhesive or the gel.

During the manufacture of the electrode plate, the combination of the sheet of metal 12, the dermally-nonirritating, adhesive, electrically conductive layer 14, and the protecting layer 20 situated below the latter layer 14 is preferably processed for instance between a set of rollers, one of the rollers being embossed in such manner that the sheet 12 is pressed down into the adhesive, electrically conductive layer at certain points for instance as indicated in FIG. 4 in a pattern with about 5 points per cm. In this manner good electric contact is assured between the two electrically conductive layers 12 and 14.

In the above, the electrode plate according to the invention has been described exemplified by some specific embodiments. However, it should be appreciated that various changes and modifications may be made without departing from the spirit and scope of the invention.

What is claimed is:

1. An electrode plate for use in connection with a defibrillation electrode, said electrode plate comprising substantially coextending inter-connected first and second electrically conductive layers, said first layer comprising raised rim means defining an area within which a defibrillation electrode may be placed in electrically conductive contact with said first layer during delivery of an electric shock and afterwards removed from electrically conductive contact with said first layer, said second layer being provided opposite to said rim means and comprising an adhesive for bringing said electrode plate into electrically conductive contact with a selected skin area, the overall extension of said electrode plate being such that when adhered to a selected skin area of a patient, a defibrillation electrode can be placed within the confines of said raised rim means without directly touching any skin portion.

2. An electrode plate according to claim 1, wherein said first layer is a metallic layer.

3. An electrode plate according to claim 2, wherein said first electrically conductive layer is a sheet of metal selected from tin, nickel, silver and aluminum or combinations thereof.

4. An electrode plate according to claim 1, wherein said second layer is a dermally non-irritating adhesive layer.

5. An electrode plate according to claim 4, wherein said dermally nonirritating layer is an electrically conductive adhesive gel.

6. An electrode plate according to claim 4, wherein said dermally nonirritating layer is an electrically conductive, pressure sensitive adhesive.

7. An electrode plate according to claim 4, wherein said dermally nonirritating adhesive layer is covered by a releasable protecting layer.

8. An electrode plate according to claim 4 or 7, wherein a section of said dermally nonirritating adhesive layer being located along an edge portion of said layer is covered by a sheet presenting a non-sticky exposed surface for providing a means for grasping the edge of the electrode plate.

9. An electrode plate according to claim 8, wherein said sheet is made from paper or a plastic material in a colour distinctly diverging from the colour of the surrounding parts of the electrode plate.

10. An electrode plate according to claim 7, wherein a combination of said first electrically conductive layer, said second electrically conductive, dermally nonirritating layer, and said protecting layer is embossed in a granular pattern in such manner that said first layer is pressed into said second layerin a plurality of small sections or locations.

11. An electrode plate according to claim 1, wherein said raised rim means is continously extending.

12. An electrode plate according to claim 1 or 11, wherein said rim means is provided by a striplike member of foamed plastics.

* * * * *

UNITED STATES PATENT AND TRADEMARK OFFICE
CERTIFICATE OF CORRECTION

PATENT NO. : 4,974,917

DATED : December 4, 1990

INVENTOR(S) : Niels Kornerup

It is certified that error appears in the above-identified patent and that said Letters Patent is hereby corrected as shown below:

In Claim 10, column 4, line 60 "layerin" should be
--layer in--

Signed and Sealed this

Twenty-fifth Day of August, 1992

Attest:

DOUGLAS B. COMER

Attesting Officer

Acting Commissioner of Patents and Trademarks